United States Patent [19]

Jung et al.

[11] Patent Number: 4,985,252

[45] Date of Patent: Jan. 15, 1991

[54] MEDICATION, DIETETIC PRODUCT AND HYGIENIC PRODUCT IN THE FORM OF A POWERED COMPOSITION OBTAINED BY ADSORPTION OF ACTIVE INGREDIENTS ON A RAPIDLY DISSOLVING SUGAR AND PROCESS FOR OBTAINING SAID COMPOSITION

[75] Inventors: Christophe Jung; Jean Jung, both of Strasbourg, France

[73] Assignee: R. I. Ph. Recherche Informatique et Pharmacie (S.A.R.L.), Strasbourg, France

[21] Appl. No.: 183,263

[22] Filed: Apr. 4, 1988

[30] Foreign Application Priority Data

Apr. 7, 1987 [FR] France ................. 87 04985

[51] Int. Cl.$^5$ .................... A61K 9/14; A61K 9/16; A61K 31/70; A61K 47/00

[52] U.S. Cl. ................. 424/439; 424/440; 514/777

[58] Field of Search ............ 514/420, 458, 777; 424/439, 440

[56] References Cited

U.S. PATENT DOCUMENTS

| | | | |
|---|---|---|---|
| 3,873,694 | 3/1975 | Kanig | 514/458 |
| 4,089,944 | 5/1978 | Thomas | 424/101 |
| 4,172,897 | 10/1979 | Ueno et al. | 424/128 |
| 4,232,012 | 11/1980 | Orr et al. | 514/420 |
| 4,303,684 | 12/1981 | Pitchun et al. | 426/312 |
| 4,349,542 | 9/1982 | Staniforth | 514/777 |
| 4,384,005 | 5/1983 | McSweeney | 426/250 |
| 4,572,916 | 2/1986 | Lindley et al. | 514/777 |
| 4,632,843 | 12/1986 | Pich et al. | 427/3 |
| 4,651,715 | 3/1987 | Breithaupt | 127/61 |
| 4,678,670 | 7/1987 | Tomic | 424/127 |
| 4,716,046 | 12/1987 | Lavie | 426/96 |
| 4,725,427 | 2/1988 | Ashmead et al. | 514/458 |
| 4,761,274 | 8/1988 | Denick, Jr. et al. | 514/960 |
| 4,772,627 | 9/1988 | Matsui et al. | 514/462 |
| 4,861,382 | 8/1989 | Goodacre et al. | 127/60 |
| 4,867,942 | 9/1989 | Gergely et al. | 424/466 |
| 4,873,085 | 10/1989 | Fuisz | 424/410 |

FOREIGN PATENT DOCUMENTS

| | | |
|---|---|---|
| 0111209 | 6/1984 | European Pat. Off. . |
| 0196813 | 10/1986 | European Pat. Off. . |
| 1667921 | 5/1970 | Fed. Rep. of Germany . |
| 1811809 | 8/1970 | Fed. Rep. of Germany . |
| 3124574 | 6/1982 | Fed. Rep. of Germany . |
| 156609 | 10/1932 | Switzerland . |
| 2086227 | 5/1982 | United Kingdom ......... 424/493 |

OTHER PUBLICATIONS

"Indomethacin-Sugar Dispersions", *Chemical Abstracts*, vol. 94, No. 18, May 1981, No. 145262n, By N. Sanghavi et al., p. 367.

"Sorbitol Instant an Excipient with Unique Tableting Properties", *Chemical Abstracts*, vol. 105, No. 232390s, By A. Basedow et al., p. 359.

*The Merck Index*, 10th Ed. (1983), p. 1273, No. 8756.

*Primary Examiner*—Shep K. Rose
*Attorney, Agent, or Firm*—Young & Thompson

[57] ABSTRACT

A powdered composition obtained by adsorption of active ingedients, previously dissolved in an organic solvent, on instant sugar, and a process for producing this composition. As a medication, it contains at least one medically active ingredient adsorbed on the external and/or internal surface of particles of an instant sugar very rapidly soluble in water.

10 Claims, No Drawings

MEDICATION, DIETETIC PRODUCT AND HYGIENIC PRODUCT IN THE FORM OF A POWERED COMPOSITION OBTAINED BY ADSORPTION OF ACTIVE INGREDIENTS ON A RAPIDLY DISSOLVING SUGAR AND PROCESS FOR OBTAINING SAID COMPOSITION

The present invention has as its object a medication, a dietetic product and a hygienic product in the form of a powdered composition obtained by adsorption of active ingredients on a rapidly dissolving sugar.

There are known at present medications, dietetic products, as well as hygienic products in the form of a powdered composition obtained by mixing one or form active ingredients with different excipients of differing nature, among them certain sugars of the sucrose, lactose or glucose type. These powders are simple mixtures used as such or incorporated in capsules or incorporated in forms such as tablets, suspensions, etc...

However, the polymorphism, the crystalline form, the particle size, the speed of dissolution of the active ingredient or ingredients has an important bearing on the pharmaceutical utility, particularly when the medication is administered by the oral route and when the active ingredient or ingredients are not completely soluble in the stomach and in the digestive tract or when the dissolution is too slow. The same is true for dietetic products and hygienic products. By thus increasing the pharmaceutical suitability of the active ingredient or ingredients, its concentration in the blood is increased with added efficacy of the product administered.

The object of the present invention is therefore to provide medications, dietetic products or hygienic products in the form of powdered compounds containing one or more active ingredients adsorbed on the external and/or internal surface of a sugar practically instantaneously soluble in water, whereby the pharmaceutical suitability of the active ingredient or ingredients is substantially superior to that of the usual form used in therapy, in dietetics, or in the field of hygienic products.

It thus has for its object a medication, in the form of a powdered composition, characterized in that it contains at least one active ingredient adsorbed on the external and/or internal surface of sugar particles "instantaneously very rapidly soluble in water."

It also has for its object a dietetic product, in the form of a powdered composition, characterized in that it contains at least one substance, "called an active ingredient," promoting the physiological equilibria of the human or animal body, adsorbed on the external and/or internal surface of particles of a sugar instantaneously very rapidly soluble in water.

Finally, it has for its object an hygienic or health care product in the form of a powdered composition, characterized in that it contains at least one substance, called an active ingredient, adsorbed on the external and/or internal surface of particles of a sugar instantaneously very rapidly soluble in water.

The active ingredient or ingredients of medical or dietetic or hygienic activity are first dissolved in an organic solvent, then are adsorbed on the external and/or internal surface of particles of sugar instantaneously after evaporation of this organic solvent, so as to obtain crystalline and/or amorphous particles and/or liquid globules of active ingredients of the desired structure and size.

According to a characteristic of the invention, there is preferably used as the instant sugar, instant sucrose. It is in fact known that this product is obtained by a special crystallization and has a large specific surface. Thanks to this, it is able to adsorb a greater quantity of active ingredients, this adsorption taking place either from a liquid active ingredient, or from an organic solution of the active ingredient. Such "instant sucrose" can be that manufactured, for example, by the company Suddeutsche Zucker-Aktiengesellschaft (West Germany) or else by the company Beghin-Say (France).

Of course, other sugars and polyhydroxyl compounds can be used, provided they are partially soluble in an organic or aqueous solvent, and preferably an ethanolic solution of variable alcoholic degree. The sugars most used at present are sucrose, glucose or lactose.

According to another characteristic of the invention, this rapidly dissoluble instant sugar can be produced conjointly with the final product by mixing, in a first step, a concentrated aqueous solution of sugar with an alcoholic solution of one or more active ingredients, then evaporating if desired under partial vacuum and/or with heating, this mixture until a powdered mixture is obtained.

According to a secondary characteristic of the invention, the compositions according to the invention contain at least one active ingredient in the form of a compound or mixture of compounds which are insoluble or difficultly soluble in water, but soluble in organic solvents. These compositions can preferably contain at least one active ingredient free from any amine group insoluble or difficulty soluble in saliva or acid medium, such as gastric juice.

According to the invention, there is also obtained one or more active ingredients in amorphous or microcrystalline form, or liquid globules, uniformly at the surface and/or the interior of particles of instant sugar.

The crystallized active ingredient examined under the microscope is seen at the outset in the form of a mixture of particles from one micron to several hundreds of microns. After adsorption on the instant sugar and dissolution in water, the active ingredient exists either in amorphous or finely divided form in the aqueous medium, or in a microcrystalline form of a maximum size of about several microns.

The dissolution of the instant sugar at the time of use gives rise to a great dispersion of the active ingredients previously adsorbed on the surface of the sugar.

The compositions according to the invention may take the form of a dry solid galenic, particularly in the form of capsules, tablets or suppositories.

In the case of a capsule, the latter may be opened at the time of use, the powder, placed on the tongue, thus promoting passage of the active ingredient or ingredients into the blood stream, the instant sugar dissolving very rapidly in the saliva.

The very rapidly dissoluble powder placed under the tongue is particularly indicated for homeopathic therapies.

The invention also has for its object a process for the obtention of a powdered composition according to the invention, consisting in dissolving at least one active ingredient in an organic solvent, mixing the organic solution obtained with instant sugar, then evaporating the organic solvent. This latter can be either an ether or preferably an ethyl ether and higher homologs, or an ester, preferably ethyl acetate and homologs, or a ketone, preferably acetone and higher homologs, or an acid, preferably acetic acid and higher homologs, or an alcohol, preferably methanol, ethanol and higher homologs, or a halogenated solvent, preferably methylene chloride, chloroform and homologous halogens, or finally a hydrocarbon solvent, preferably hexane, toluene and homologs.

According to a modified form of the invention, the process consists in reacting an ethereal solution of vitamin E, the principal active ingredient, with instant sugar, then letting the solvent evaporate until it is completely eliminated and obtaining a powdered mass.

According to a second modified form of the invention, the process consists in reacting one or more essential oils used in aroma therapy with the instant sugar.

According to a third modified form of the invention, the process consists in reacting a methylene chloride solution of indomethacin with the instant sugar, and evaporating the organic solvent.

The invention will be better understood from the following non-limiting examples:

EXAMPLE 1

100 g of sucrose solution (67 g sucrose and 33 g water) are mixed with 300 ml of an ethanolic solution of indomethacin (6.70 g indomethacin dissolved in 295 ml ethanol 95°). The solvents are evaporated under vacuum of about 20 mm Hg. The powder is homogenized and capsules are prepared containing 275 mg of powder. The sugar has lost its usual crystalline appearance.

EXAMPLE 2

2.5 g of indomethacin are dissolved in 100 ml of methylene chloride and mixed with 25 g of fine instant sugar (reference 4515) prepared by the company Suddeutsche-Aktiengesellschaft, Werk Wagheusel. The material is thoroughly mixed and the solvent is evaporated. The powder is homogenized and capsules are prepared containing 275 mg of powder (active ingredient per capsule: 25 mg indomethacin).

EXAMPLE 3

3 g of vitamin E are dissolved in 100 ml of ethyl ether and mixed with 20 g of instant sugar (reference 4515) prepared by the company Suddeutsche-Aktiengesellschaft. The mixture is thoroughly mixed and the solvent evaporated. The powder is homogenized and capsules are prepared containing 230 mg of powder (active ingredient per capsule: 30 mg of vitamin E).

EXAMPLE 4

1 g of tincture of Arnica is titrated with 9 g of instant sugar. 1 g of this titer is removed and mixed with 9 g of instant sugar. 1 g of this second dilution is titrated with 9 g of instant sugar; there is thus obtained a third decimal dilution which is instant sugar based Arnica, a preparation very rapidly dissolved after sublingual administration. By identical successive dilutions, there are thus obtained predetermined dilutions for homeopathic treatments. The powder may be supplied in capsules which are opened at the time of use, the powder being placed under the tongue.

All homeopathic tinctures may thus be formulated as homeopathic preparations.

EXAMPLE 5

750 mg of each of the essential oils lavender, savory, basil and caraway (essential oils which are known for the treatment of intestinal afflictions, enteritis, colitis, parasitosis, as described in the work of Dr. J. Valnet "Aroma Therapy Treatment of Maladies by Plant Essences", Maloine Ed. 1981, page 368) are dissolved in 20 ml of ether and mixed with 18 g of instant sugar. This is thoroughly mixed and the solvent evaporated. The powder is homogenized and capsules are prepared containing 300 mg of powder.

The quantity of adsorbable ingredient depends on each case in question; this quantity may easily be 10 to 20% relative to the instant sugar and may in certain cases be more.

It follows that the proportions of the quantities employed in Examples 1 to 5 are convertible to an industrial scale of hundreds of kilograms, the adsorption not being changed.

After oral administration of 50 mg of indomethacin (2 capsules of 25 mg), the blood is collected and 5 ml of plasma are extracted three times with 5 ml of ether. After evaporation of the solvent, the residue is recovered with 0.1 ml of ethanol. After separation by thin layer chromatography and quantitative analysis by densitometry, it is found that the pharmaceutical availability is improved for indomethacin adsorbed on instant sugar, as evidenced by the presence of $2.5 \pm 0.36$ $\mu g/ml$, one hour after administration, for indomethacin adsorbed on instant sugar at $1.35 \pm 0.31$ $\mu g/ml$ for capsule form utilized in therapy or $2.2 \pm 0.37$ $\mu g/ml$ two hours after administration for indomethacin adsorbed on instant sugar at $1.3 \pm 0.54$ $\mu g/ml$ for capsules utilized in therapy.

Of course, the invention is not limited to the embodiments described and explained above. Modifications are possible, particularly as to the constitution of the various elements or by substitution of technical equivalents, without thus departing from the field of protection of the invention.

We claim:

1. A powdered composition, characterized in that it consists essentially of at least one medically active ingredient adsorbed on the external and/or internal surface of particles of instant sugar selected from the group consisting of sucrose, glucose and lactose, produced by evaporating an organic solvent solution of said active ingredient containing said instant sugar dispersed therein, said organic solvent solution comprising an organic solvent not dissolving said instant sugar.

2. Composition according to claim 1, wherein said at least one medically active ingredient is a compound insoluble in water, but soluble in organic solvents.

3. Composition according to claim 1, which contains at least one active ingredient free from an amino group, said at least one compound being insoluble in saliva or acid medium.

4. Composition according to claim 1 in which said at least one active ingredient is in amorphous or microcrystalline form or in the form of liquid globules, uniformly distributed at the surface and/or the interior of particles of instant sugar.

5. Composition according to claim 1 in the form of a dry solid galenic.

6. Process for the production of a powdered composition consisting essentially of dissolving at least one medically active ingredient in an organic solvent, mixing the organic solvent solution obtained with instant sugar selected from the group consisting of sucrose, glucose and lactose, said organic solvent not dissolving said instant sugar, then evaporating the organic solvent.

7. Process according to claim 6, which comprises reacting an ether solution of vitamin E, as liquid active ingredient, with instant sugar, then evaporating the solvent until it is completely eliminated and obtaining a pulverulent mass.

8. Process according to claim 6, in which at least one essential oil used in aroma therapy are admixed with the instant sugar.

9. Process according to claim 6, in which a methylene chloride solution of indomethacin is admixed with the instant sugar, and evaporating the organic solvent.

10. Process according to claim 6, in which as organic solvent there is used a member selected from the group consisting of an ether, and ester, a ketone, an acid, an alcohol, a halogenated solvent, and a hydrocarbon solvent.

* * * * *